(12) United States Patent
Alshail

(10) Patent No.: US 11,464,538 B2
(45) Date of Patent: Oct. 11, 2022

(54) SURGICAL APPARATUS, IN PARTICULAR A NAVIGATION PROBE FOR LOCALIZING AND TREATING LESIONS IN A BRAIN

(71) Applicant: KING FAISAL SPECIALIST HOSPITAL & RESEARCH CENTRE, Riyadh (SA)

(72) Inventor: Essam Abdulaziz Alshail, Riyadh (SA)

(73) Assignee: KING FAISAL SPECIALIST HOSPITAL & RESEARCH CENTRE, Riyadh (SA)

( * ) Notice: Subject to any disclaimer, the term of this patent is extended or adjusted under 35 U.S.C. 154(b) by 0 days.

(21) Appl. No.: 16/744,641

(22) Filed: Jan. 16, 2020

(65) Prior Publication Data
US 2020/0146713 A1    May 14, 2020

Related U.S. Application Data

(63) Continuation of application No. 15/669,905, filed on Aug. 5, 2017, now Pat. No. 10,828,062, which is a (Continued)

(51) Int. Cl.
*A61B 17/34* (2006.01)
*A61B 90/50* (2016.01)
(Continued)

(52) U.S. Cl.
CPC .......... *A61B 17/3403* (2013.01); *A61B 90/11* (2016.02); *A61B 90/39* (2016.02); *A61B 90/50* (2016.02); *A61B 8/4209* (2013.01); *A61B 2017/3405* (2013.01); *A61B 2017/3407* (2013.01); *A61B 2017/3409* (2013.01); *A61B 2034/2051* (2016.02); *A61B 2034/2055* (2016.02)

(58) Field of Classification Search
CPC ..... A61B 8/42; A61B 8/4209; A61B 17/3403; A61B 2017/320052; A61B 2017/3405; A61B 2017/3407; A61B 2017/3409; A61B 90/11; A61B 90/50
See application file for complete search history.

(56) References Cited

U.S. PATENT DOCUMENTS 4,877,033 A   10/1989   Seitz, Jr.
5,280,427 A   1/1994    Magnusson et al.
(Continued)

*Primary Examiner* — Todd J Scherbel
(74) *Attorney, Agent, or Firm* — Saliwanchik, Lloyd & Eisenschenk

(57) ABSTRACT

The invention relates to a surgical apparatus, in particular a navigation probe for localizing and treating lesions in a brain, comprising a telescopically expandable body member having an anterior end, a posterior end, and comprising a top part and a bottom part, the bottom part having at least one groove extending for a particular length in a longitudinal direction of the bottom part between said anterior end and said posterior end, the top part being placed on said bottom part and having at least one engaging element that extends into said at least one groove so as to mount the top part on the bottom part moveable in said longitudinal direction, wherein the body member has a substantially circular or polygonal cross-section in the assembled state of the bottom part and the upper part.

13 Claims, 9 Drawing Sheets

Related U.S. Application Data continuation of application No. 14/335,417, filed on Jul. 18, 2014, now Pat. No. 9,750,531.

(51) Int. Cl.
*A61B 90/00* (2016.01)
*A61B 90/11* (2016.01)
*A61B 8/00* (2006.01)
*A61B 34/20* (2016.01)

(56) References Cited

U.S. PATENT DOCUMENTS

| | | |
|---|---|---|
| 5,704,900 A | 1/1998 | Dobrovolny et al. |
| 6,132,431 A | 10/2000 | Nilsson et al. |
| 6,267,770 B1 | 7/2001 | Truwit |
| 6,371,973 B1 | 4/2002 | Tepper |
| 6,859,660 B2 | 2/2005 | Vilsmeier |
| 7,803,137 B2 * | 9/2010 | Stefanchik ......... A61B 1/00073 604/174 |
| 8,444,566 B2 | 5/2013 | Agmon |
| 8,574,160 B2 | 11/2013 | Gorzitze |
| 9,748,421 B2 | 8/2017 | Mitra et al. |
| 9,750,531 B2 | 9/2017 | Alshail |
| 2015/0272694 A1 | 10/2015 | Charles |

* cited by examiner

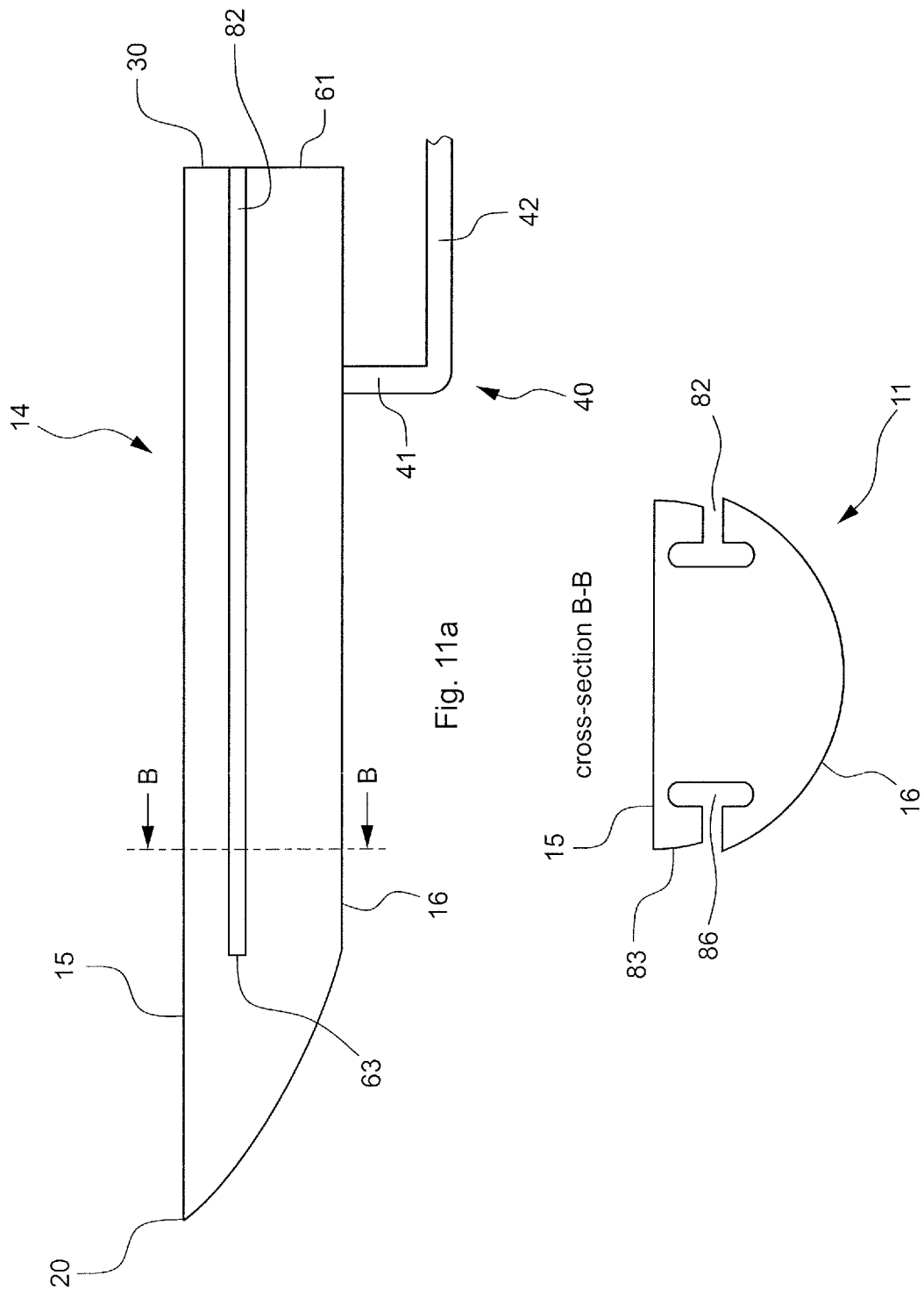

SURGICAL APPARATUS, IN PARTICULAR A NAVIGATION PROBE FOR LOCALIZING AND TREATING LESIONS IN A BRAIN

CROSS-REFERENCE TO A RELATED APPLICATION

This application is a Continuation-In-Part application of Ser. No. 15/669,905, filed Aug. 5, 2017; which is a Continuation Application of U.S. application Ser. No. 14/335,417, filed Jul. 18, 2014, now U.S. Pat. No. 9,750,531, all of which are incorporated herein by reference in their entirety.

FIELD OF THE INVENTION

The invention relates to a surgical apparatus, in particular a navigation probe for localizing and treating lesions in a brain.

BACKGROUND OF THE INVENTION

Computer-assisted surgery (CAS) represents a surgical concept and a set of methods that use computer technology for pre-surgical planning, and for guiding or performing surgical interventions. CAS is also known as Computer Aided Surgery, Computer Assisted Intervention, Image Guided Surgery and Surgical Navigation.

In computer-assisted surgery, the actual intervention is defined as surgical navigation. Using a surgical navigation system the surgeon will use special instruments, which are connected to the navigation system to approach an anatomical position within the patient. This position is simultaneously shown in the images taken from the patient. The surgeon can thus use the instrument to navigate the images of the patient by moving the instrument. Computer-Assisted neurosurgery telemanipulators allowed a greater development in brain microsurgery by compensating the surgeon's physiological tremor by 10-fold, thereby increasing the accuracy and precision of the intervention. It also opened a new gate to minimally invasive brain surgery, furthermore reducing the risk of post-surgical morbidity by accidentally damaging adjacent centers.

In the prior art, there are various instruments and devices for guiding medical instruments and devices into the body either for diagnostic or therapy purposes. U.S. Pat. No. 5,280,427 A discloses an apparatus for guiding the needle of a tissue sampling device to a target location within the body of a patient. The device is adapted to permit accurate and easy retrieval of acceptable tissue specimens from locations within the body of the patient, which require angling of the needle to reach the target tissue.

Further, U.S. Pat. No. 8,574,160 B2 discloses a needle guide system for a sonography device including both fixed and adjustable needle guides, which may include a needle guide body that is rotatably mounted to a probe of a sonography device.

U.S. Pat. No. 4,877,033 A discloses a completely disposable apparatus of single unit construction designed for operative use in conjunction with a transvaginal ultrasound probe when performing transvaginal surgical procedures with ultrasonic guidance. The apparatus includes a probe covering sheath containing a probe securing mechanism, an instrument or needle guide, and an ultrasound cable sleeve.

U.S. Pat. No. 6,267,770 B1 discloses a surgical apparatus for accurately aligning the trajectory of, guiding of, and introducing or withdrawal of an instrument. The apparatus includes a base comprising a moveable member moveably attached to the base. The moveable member has a passage therein which forms a portion of the trajectory path. A positioning stem further includes a first locator and a second locator. The first and second locators are associated with two different portions of the positioning stem so that they are essentially two points on a line. The first and second locators are also locatable by a scanning or an imaging system.

U.S. Pat. No. 8,444,566 B2 discloses an apparatus for detecting an environment within a body comprising a stylet and a catheter capable of being inserted into the body, and a bio-sensing module for detecting a predefined material within the body.

U.S. Pat. No. 6,859,660 B2 discloses a Neuro-navigation system comprising a reflector referencing system including passive reflectors and a marker system with markers or landmarks, wherein the reflectors as well as the markers as regards their shape, size and material selection as well as their arrangement or attachment on the parts of the body to be operatively treated and on the surgical instruments are configured so that mapping their locations is substantially facilitated or is able to take place more accurately positioned by a computer/camera unit having a graphic display terminal as well as the operative treatment with the aid of this unit.

The aforementioned devices from the prior art are adapted for localizing the position of the probe. However, it is desirable that such systems and devices are also adapted for guiding any other medical instruments or devices like devices for treating lesions in a brain.

BRIEF SUMMARY

It is therefore an object of the invention to provide a surgical apparatus as mentioned above that allows to act as a guide for instruments or devices to be inserted in the body of a patient for diagnostic or treatment purposes, in particular for medical devices for the treatment of lesions in a brain.

This object is solved by an apparatus comprising the features of claim 1. The depending claims 2 to 15 each refer to a preferred embodiment of the inventive apparatus.

BRIEF DESCRIPTION OF THE FIGURES

More details on the inventive concept are discloses with respect to the following figures showing preferred embodiments. Therein, FIG. 1—discloses a side view of a first embodiment of the inventive surgical apparatus;

FIG. 9—an embodiment of the inventive surgical apparatus for static mounting on an operation table or the like;

FIG. 10*b*—a cross sectional view of the top part of the body member according to FIG. 10*a*;

FIG. 11a—a side view of the bottom part of the two-part version of the body member;

FIG. 11b—a cross sectional view of the bottom part of the body member according to FIG. 11a;

FIG. 12a—a side view of the connected bottom part and top part of the two-part version of the body member;

FIG. 12b—a cross sectional view of the connected top and body part of the two part version of the body member according to FIG. 12a;

DETAILED DESCRIPTION

Figure 1:
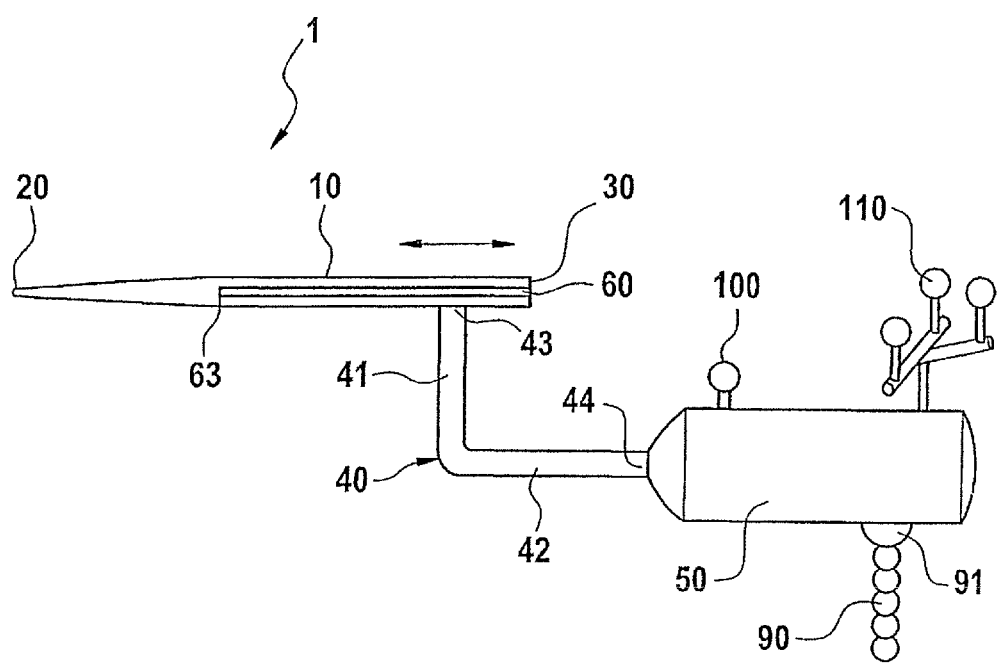

According to the present invention, the surgical apparatus comprises a body member having an anterior end, a posterior end, and at least one groove extending for a particular length in a longitudinal direction of the body member between said anterior end and said posterior end. The apparatus further comprises a saddle that is adapted to securely hold a medical device, wherein the saddle is placed on said body member having at least one grip that extends into said at least one groove so as to mount the saddle on the body member moveable in said longitudinal direction. The inventive apparatus furthermore includes a means for maneuvering said body member.

Thus, the inventive concept is based on the idea to provide a saddle and a body member, wherein the saddle is slidingly mounted on the body member and therefore allows for displacement of a treatment and/or diagnostic that is fixed or mounted to or in the saddle. Preferably, the sliding connection between the saddle and the body member is adapted for high precision displacement of the saddle with respect to the body member. The mean function of the grooves is therefore to provide secure path of the treatment and/or diagnostic device or devices mounted on or in the saddle during the introduction and withdrawal of these devices.

The as least one groove could have different forms, for example a round shape, or could have sharp edges, or could be formed like a railway track. The number of grooves is preferably from at least one groove till three grooves, wherein in or on the saddle one or more devices can be mounted.

According to an embodiment of the invention said at least one groove comprises an inner shape and said at least one grip comprises an outer shape, wherein said inner shape and said outer shape are form-locking or essentially form-locking with respect to each other and are slidingly supported on one another. By means of the form-locking shapes of the groove and the grip, respectively, both components may be displaced with respect to each other in a highly precise manner.

According to another embodiment said inner shape and said outer shape of the groove and the grip, respectively, form an undercut and monovariant connection between said at least one groove and said at least one grip. The Undercut allows secure hold of the saddle on the body member, while the monovariant connection allows precise adjustment of the saddle with respect to the body member.

In order to achieve that the saddle comprises at least one defined longitudinal position with respect to the body member, according to an embodiment of the invention said at least one groove comprises a block. Said block may be located at the groove's end facing the anterior end of the body member. In an embodiment an end of the groove facing the anterior end of the body member forms the block.

The exchange of the saddle is simplified in another embodiment of the invention by providing the at least one groove of the body member with an insert opening at the front face of the posterior end of the body member. Preferably, the saddle is adapted to hold at least one particular medical device, so that that the saddle might have to be exchanged by another saddle in order to convert the surgical apparatus to hold a different medical device.

According to another embodiment the body member is wider on the posterior end than on the anterior end. The at least one groove may be formed in a section of the body member comprising a constant cross section in longitudinal direction, wherein the groove ends right before or nearby a transitional area where the cross section of the body member narrows in direction of the anterior end.

In a preferred embodiment the body member comprises two of said grooves, one groove on each of two opposite longitudinal outer faces of the body member. In this embodiment, the saddle comprises preferably two grips, one grip on each of two opposite longitudinal inner faces of the saddle, so that each of said grips engages one of said grooves of the body member.

The saddle may comprise various shapes, wherein each particular shape is adapted to an outer contour of a medical device to be connected with the surgical apparatus. In an embodiment the saddle comprises an open cylinder adapted for mounting a medical device.

In another embodiment the saddle comprises a closed cylinder adapted for mounting a medical device. In still another embodiment the saddle comprises at least one of each, an open cylinder and a closed cylinder, each cylinder having a specific contour for adaption of medical device.

In the embodiment wherein said saddle comprises an open cylinder, said open cylinder may have two wings spaced apart by an arch, wherein the free ends of said wings form an opening of the open cylinder for insertion of a medical device, and wherein said opening extends in the longitudinal direction.

Preferably, said arch and said wings form a receptacle for a medical device, wherein said receptacle has an inner and/or outer contour adapted to an inner and/or outer contour of a medical device to be mounted in the open cylinder.

According to another embodiment of the invention the means for maneuvering said body member comprise a handle and a neck having a vertical arm and a horizontal arm, wherein the neck connects the handle with the body element. The vertical arm has a proximal part connecting to the body element, and the horizontal arm has a distal part connecting to the handle.

The handle may comprise reflection balls for optical navigation and/or electromagnetic sensors for electromagnetic navigation.

The inventive surgical apparatus may be designed as a portable and hand held device or as a static device. In and embodiment of a static surgical apparatus according to the present invention, the handle is mounted on a flexible arm adapted to be fixed to a stationary device, in particular to an operation table. In an embodiment thereof a proximal part of the flexible arm may be connected or fixed to a handle of the surgical apparatus by means of at least one proximal clamp, wherein a distal part of the flexible arm is connected or fixed to the stationary device by means of at least one distal clamp.

According to another embodiment of the invention the surgical apparatus, in particular the navigation probe for localizing and treating lesions in a brain, can comprise a telescopically expandable body member having an anterior end a posterior end, wherein the body member can comprise a top part and a bottom part. The bottom part can have at least one groove extending for a particular length in a longitudinal direction of the bottom part between said anterior end and said posterior end. The top part can be placed on said bottom part and can have at least one engaging element that extends into said at least one groove so as to mount the top part on the bottom part moveable in said longitudinal direction. In particular, the body member can have a substantially circular or polygonal cross-section in the assembled state of the bottom part and the upper part.

Preferably, the at least one groove of the bottom part can comprise an inner shape and said at least engaging element of the top part can comprise an outer shape, wherein said inner shape and said outer shape are form-locking with respect to each other and are slidingly supported on one another.

Further, said inner shape and said outer shape can form an undercut and monovariant connection between said at least one groove of the bottom part and said at least one engaging element of the top part.

Moreover, the at least one engaging element of the top part can comprise a leg extending downwardly away from said top part, and a T-shaped base element extending horizontally from the end of the leg to the inside of the top part. Thereby, the outer surface of the downwardly extending leg can define the outer contour of the circular or polygonal cross-section of the body member. Accordingly, the bottom part can comprise at least one recessed area with respect to its semi-circular outer contour to make room for the at least one leg of the top part. Due to this interaction between the leg of the top and the recessed portion of the bottom part, the round or polygonal cross-section of the body member can be achieved when the bottom and top parts are in the joined state.

Furthermore, said at least one groove of the bottom part can comprise a block at its end facing the anterior end of the body member.

The at least one groove of the bottom part can comprise an insert opening at a front face of the posterior end.

Preferably, the body member is wider on the posterior end than on the anterior end. In particular, the body member formed of the assembled top part and bottom part, which each can have flat or at least form fitting top and bottom sides assigned to each other, tapers towards the tip. The tapering preferably begins at the level of the block in the longitudinal direction and ends at the tip of the body member.

In particular, said bottom part can comprise two of said grooves, one groove on each of two opposite longitudinal outer faces of the bottom part. The grooves each can consist of a horizontal and a vertical section which are arranged perpendicular to each other. Preferably, the grooves are arranged in a T-shape to each other such that the horizontal groove section faces the outer circumference of the bottom part and the vertical groove section is positioned in the inside of the bottom part.

Further, the top part can comprise at least one groove extending for a particular length in a longitudinal direction of the top part between said anterior end and said posterior end. The groove preferably has an insert opening accessible over the face side at the posterior end of the top part. The groove extends from the insert opening to a block, the block being located at the same level as the block of the groove of the bottom part.

The surgical apparatus according to the two-part version of the body member further can comprise a saddle adapted to securely hold a medical device, the saddle being placed on said top part and having at least one grip that extends into said at least one groove of the top part so as to mount the saddle on the top part moveable in said longitudinal direction.

Alternatively, the surgical apparatus can comprise a first hollow cylinder adapted to extend the range of the surgical apparatus, the first hollow cylinder being arranged around said body member and having at least one engaging element on its inner circumference, the engaging element extending into said at least one groove of the top part so as to mount the first hollow cylinder on the body member moveable in said longitudinal direction. Preferably, the first hollow cylinder can comprise two engaging elements opposite to and facing each other. Accordingly, the top part can comprise two opposite grooves. The connection between engaging element and groove can be formed as a tongue and groove connection. More particular, the connection can comprise undercut grooves and corresponding T-shaped engaging elements.

Furthermore, the first hollow cylinder can comprise at least one groove extending for a particular length in a longitudinal direction at the outer circumference of the first hollow cylinder. Preferably, the first hollow cylinder comprises two opposite grooves at its outer circumference.

Moreover, the surgical apparatus can comprise a second hollow cylinder, the second hollow cylinder being arranged around the first hollow cylinder and having at least one engaging element on its inner circumference, the engaging element extending into said at least one groove of the first hollow cylinder so as to mount the second hollow cylinder on the first hollow cylinder moveable in said longitudinal direction. The connection between the engaging elements of the second hollow cylinder and the grooves of the first cylinder can be formed as a groove and tongue connection or moreover, can comprise undercut grooves and corresponding T-shaped engaging elements.

Further, the second hollow cylinder can comprise at least one groove extending for a particular length in a longitudinal direction at the outer circumference of the second hollow cylinder. Preferably, the second hollow cylinder comprises two opposite grooves at its outer circumference.

In order to maximize the range of the surgical apparatus, the apparatus can comprise a third or even more hollow cylinders. The third hollow cylinder can be arranged around the second hollow cylinder and can have at least one engaging element on its inner circumference. The engaging element can extend into said at least one groove of the second hollow cylinder so as to mount the third hollow cylinder on the second hollow cylinder moveable in said longitudinal direction. On the outer circumference of the outermost hollow cylinder, grooves or equivalent elements can be provided to hold a saddle adapted to securely hold a medical device according to the preceding embodiments of the invention. The hollow cylinders each can comprise an opening in form of an elongated slot in the longitudinal direction at their undersides. The openings of the cylinders are aligned to each other such that the cylinders leave space for the neck at which the bottom part of the body member is mounted.

FIG. 1 shows an embodiment of the inventive surgical apparatus 1 comprising a body member 10 that is mounted by means of a neck 40 to a handle 50, wherein the handle 50 comprises a flexible arm 90 that is mounted with its proximal end 91 to the handle 50. The neck 40 comprises a rectangular shape having a vertical arm 41 and a horizontal arm 42. The proximal end 43 of the vertical arm 41 is mounted to the body member 10 at its posterior end 30. The horizontal arm 42 of the neck 40 is mounted via its distal end 44 to the handle 50.

For the sake of better illustration no saddle is mounted on the body element 10. Preferred designs of the body element 10 and corresponding saddles are shown in the following figures. FIG. 1 further shows that the body element 10 comprises a groove 60 that extends in longitudinal direction indicated by the double arrow. The groove 60 extends from the face side 61 at the posterior end 30 of the body member 10 and in longitudinal direction of the body member 10 until a block 63 is reached. The block 63 is located in a transitional area, in which the outer contour of the body element 10 narrows until it reaches the form of a tip at the anterior end 20 of the body member 10.

The handle 50 comprises reflection balls 100, 110 for optical navigation. Such reflection balls 100, 110 are well known from the prior art. Further, but not shown, the handle may comprise electromagnetic sensors for electromagnetic navigation. Such electromagnetic navigation systems are also well known from the prior art.

Figure 2:
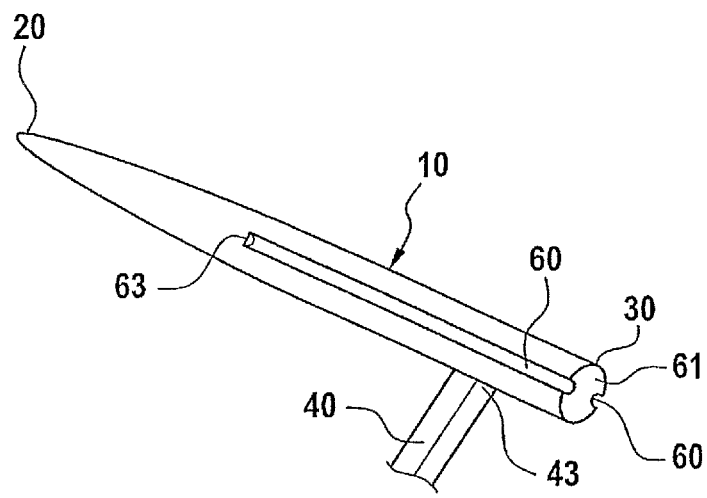
FIG. 2—a perspective view of the body member according to FIG. 1.

FIG. 2 shows a detailed view of the body member 10 according to FIG. 1. In the perspective view of FIG. 2 it may be seen that the body member 10 comprises an essentially round cross section, wherein the body member 10 comprises on each of two opposite faces a groove 60 that extends from the face side 61 at the posterior end 30 of the body member 10 until it reaches the block 63. This allows that a saddle (not shown) may be inserted on the body member 10 by introducing the grips of the saddle (not shown) from the face side 61 into the grooves 60.

Figure 3:
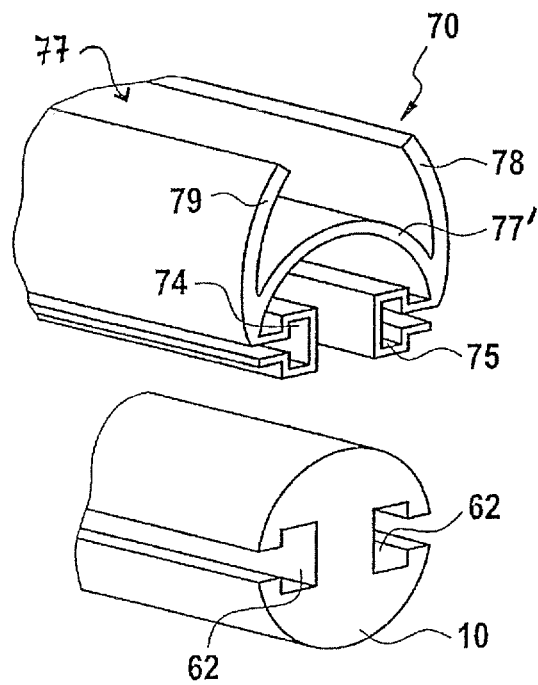
FIG. 3—a perspective view of a first embodiment of a saddle with corresponding body member.

FIG. 3 shows a first embodiment of a saddle 70 with corresponding body member 10. The saddle 70 comprises an open cylinder 77 having two wings 78, 79 located opposite to each other and forming an opening for insertion of a medical device. The bottom side of the cylinder 77 is formed by an arch 77' connecting the wings 78, 79. The arch 77' comprises an outer shape that is reproducing the outer shape of the body element 10 so that the saddle 70 may be securely placed on the body element 10.

While the body element 10 comprises on each of two opposite faces a groove 62, the saddle 70 comprises correspondingly on each of two opposite faces a grip 74, 75 that is oriented in direction of the body element 10 and engaging the grooves 62. In order to ensure that the saddle 70 may be displaced in a precise manner with respect to the body element 10, the grips 74, 75 fit form-locking into the grooves 62.

While in the embodiment according to FIG. 2 the grooves 62 comprise a round shape, in the embodiment according to FIG. 3 the grooves 62 comprise the shape of a railway track or a T-shape. The embodiment of FIG. 3 has the advantage that the shape of the grooves 62 form an undercut, so that the saddle 70 is securely held on the body element 10.

In the embodiment according to FIG. 4 the saddle 70 again comprises an open cylinder 77 with two opposite wings 78, 79 that are connected by an arch 77'. The grips 75 show the form of a dove tail, while the body element 10 comprises correspondingly formed grooves 65. Like in the embodiment of FIG. 3, the grips 75 and grooves 65 of the embodiment according to FIG. 4 form a key and slot connection. The embodiment of FIG. 7 differs from the embodiment according to FIG. 4 in such a way that the wings 78, 79 are designed differently in order to receive differently formed medical devices.

Figure 5:
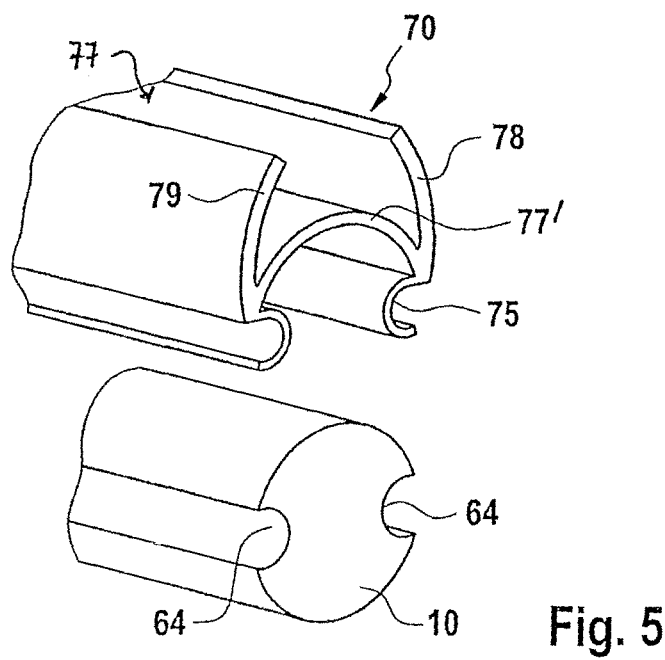
FIG. 5—a perspective view of a third embodiment of the saddle with corresponding body member.

In the embodiment according to FIG. 5 the grips 75 and the grooves 64 comprise a round shape, which may or may not form an undercut.

Figure 6:
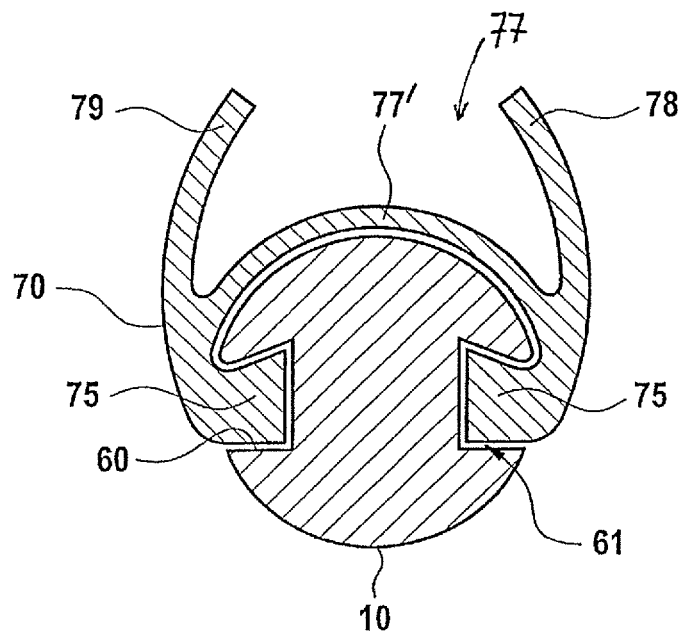
FIG. 6—a cross sectional view of a forth embodiment of a saddle with corresponding body element.

In the cross sectional view according to FIG. 6 it is shown that the saddle 70 is mounted form locking on the body element 10. On the one hand, the bottom side of the arch 77' reproduces the outer shape of the body element 10. On the other hand the outer contour of the grips 75 is adapted to fit form locking in the grooves 60, 61.

Figure 4:
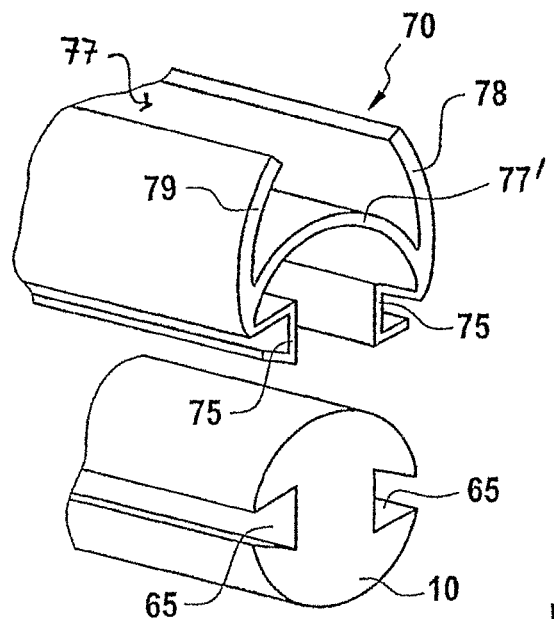
FIG. 4—a perspective view of a second embodiment of the saddle with corresponding body member.
Figure 7:
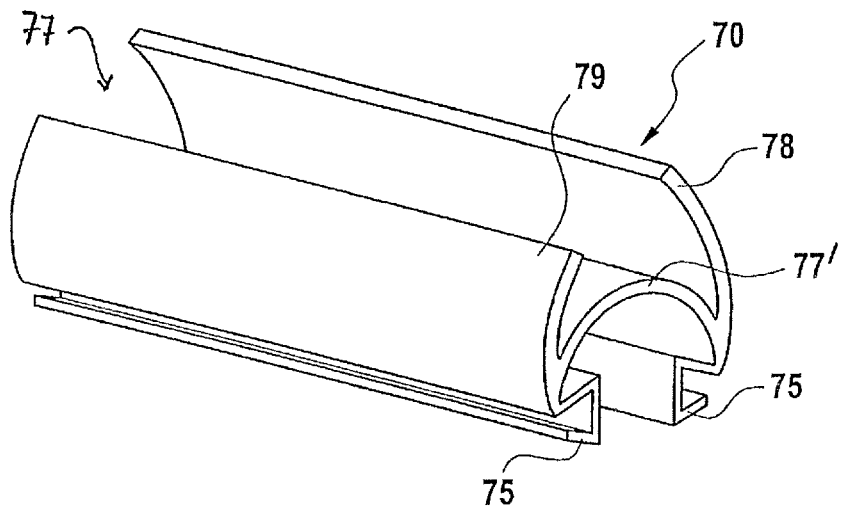
FIG. 7—a perspective view of a fifth embodiment of a saddle.
Figure 8:
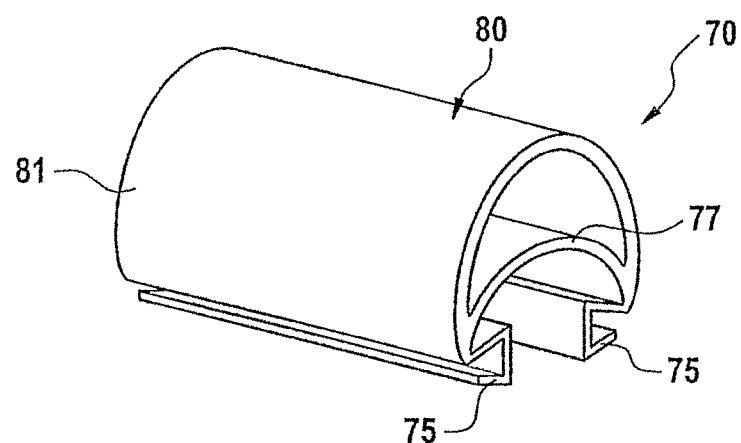
FIG. 8—a perspective view of a sixth embodiment of the saddle.

The embodiment according to FIG. 8 differs from that shown in FIGS. 4 and 7 in such a way that the shown saddle 70 comprises a closed cylinder 80 having a cavity between an outer cylinder wall 81 and the arch 77'. The cavity may be used for insertion of a medical device in such a way that the medical device is securely mounted on the saddle 70.

Figure 9:
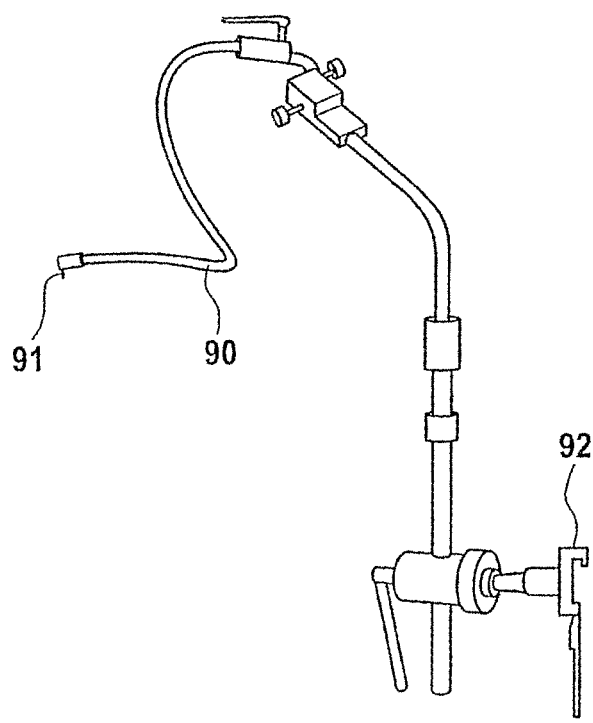

As shown in FIG. 9 the inventive surgical apparatus may comprise a flexible arm 90 having a proximal clamp 91 that is mounted to the handle 50 of the surgical apparatus (see FIG. 1). The flexible arm 90 further comprises a distal clamp 92 for mounting the flexible arm 90 on an operation table or the like. The flexible arm 90 comprises a variable shape and form and may be made from different types of material like metal or plastic.

FIGS. 10 to 13 show another embodiment of the invention according to which the body member 10 is realized as a two-part version comprising a top part 11 and a bottom part 14 which can be connected by engaging elements 67 of the top part 11 engaging in grooves 62 of the bottom part 14 and as described in detail below.

Figure 10A:
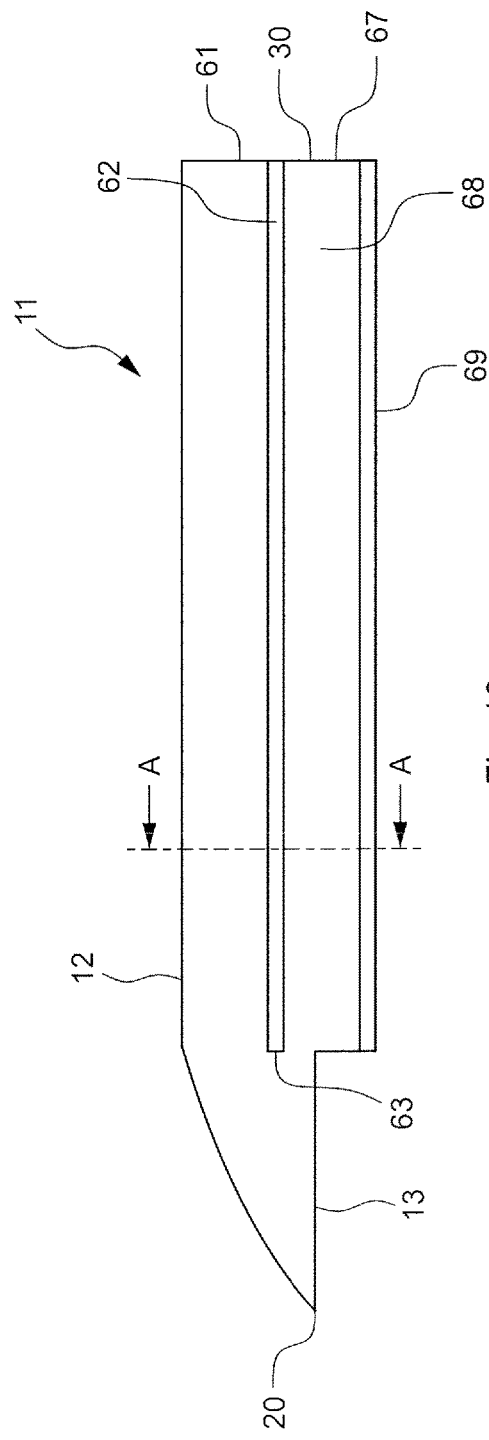
FIG. 10*a*—a side view of an embodiment of the top part of a two-part version of the body member.

FIG. 10a shows the top part 11 of the body member 10 which comprises two lateral grooves 62 which have an insert opening end at the front face 61 of the posterior end 30 of the body member 10 and a closed end bordered by block 63. To connect the top part 11 with the bottom part 14, the top part 11 has engaging elements 67 on its underside, which extend downwards from top part 11. The engaging elements 67 extend in the longitudinal direction of the top part 11 from the posterior end 30 of the top part 11 to the end of the groove 62 so that the engaging elements 67 are aligned with the block 63. The top part 11 is essentially semicircular with an arched top side 12 and a flat underside 13. Also in this embodiment, block 63 is located in a transition area in which the outer contour of the arched upper side 12 tapers downwardly towards the tip 20 of upper part 11. On the other hand, the underside 13 of the top part 11 runs flat to the tip 20.

Figure 10B:
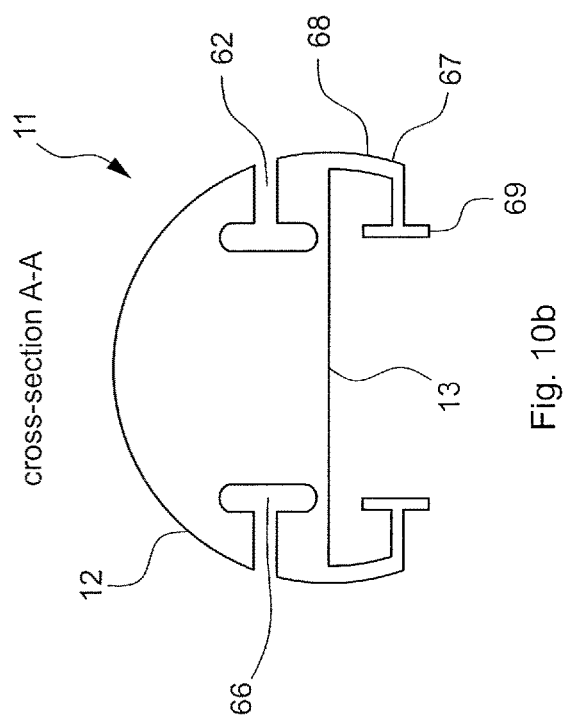

FIG. 10b shows a cross-sectional view of the top part shown in FIG. 10a. It can be seen that the top part 11 has a substantially circle-shaped outer contour. On the underside of top part 11, engaging elements 67 extend downwardly away from the flat underside 13 of top part 11. The engaging elements 67 each have legs 68 which are essentially vertical respectively follow the circular outer contour. From the ends of the legs 68, T-shaped base elements 69 each extend towards each other and towards the inside of the upper part 12, respectively. FIG. 10b also shows that the lateral grooves 62 of the upper part have an undercut 66 in which the upper bar of the T engages.

FIG. 11a shows a side view of the bottom part 14 of the two-part body part 10, which corresponds to the shape of the top part 11. The bottom part 14 has a flat upper side 15 and a semi-circular lower side 16. Like the top part 11, the bottom part 14 also has lateral grooves 82, each of which has an undercut 86. The vertical arm 41 of the neck 40, from which the horizontal arm 42 extends, is attached to the underside 16 of the bottom part 14. The side grooves 82 of the bottom part 14 also have an open end at the posterior part 30 and are closed at their opposite end by block 63. At the level of block 63, the outer contour of the bottom part 14 begins to taper upwardly towards tip 20, opposite to the contour of upper part 11. Lower part 14 has recesses 83 for the legs 68 of upper part 11 in the area above the grooves 82, so that the T-shaped base elements 69 can engage in the undercut grooves 82.

Figures 12A, 12B:
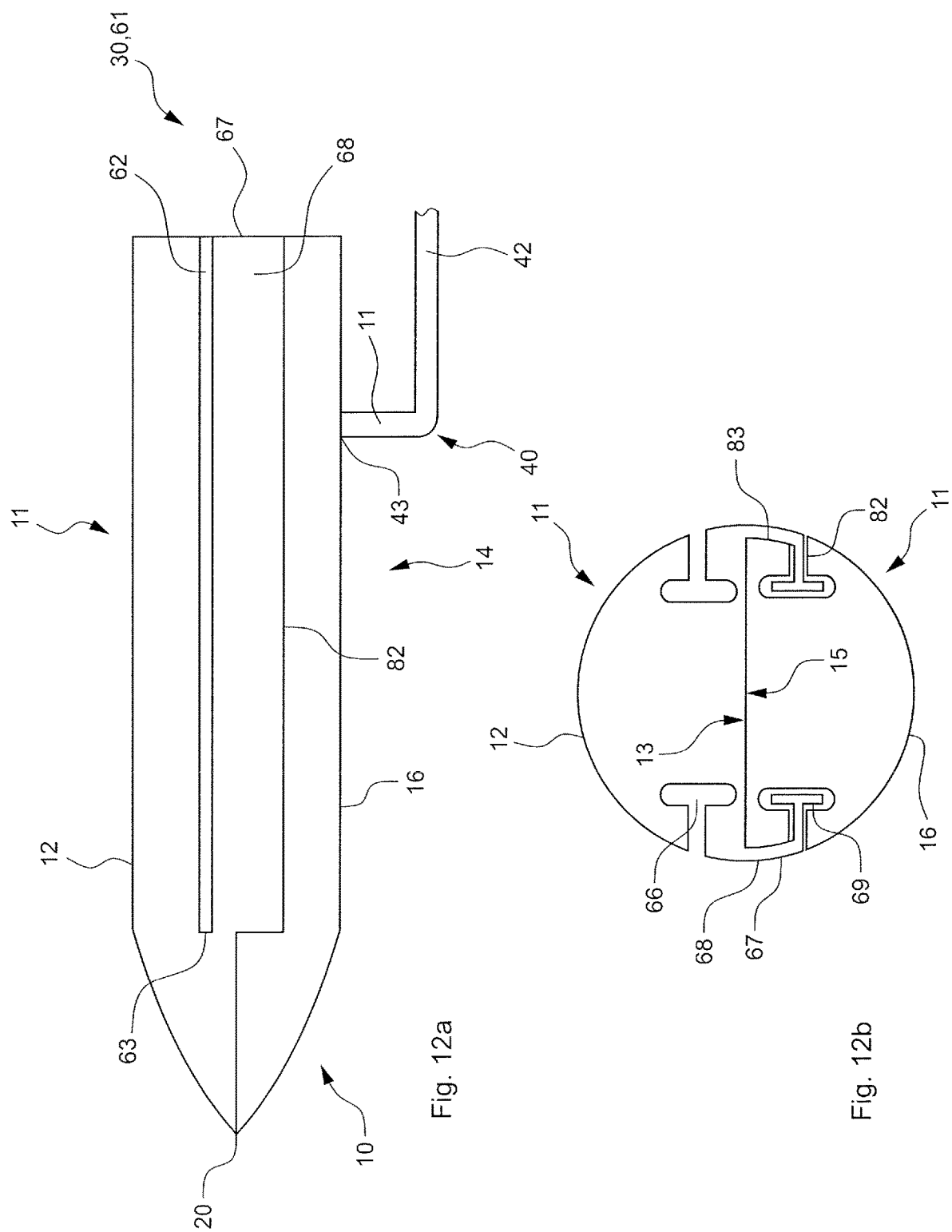

FIGS. 12a and 12b each show the body member 10 in an assembled state. To connect the bottom part 14 with the top part 11, the engaging elements 67 of the top part 11 are pushed from the rear end 30 of the lower part 14 into the undercut grooves 82 of the lower part 14 until the engagement elements 67 reach the blocks 63 of the lower part 11. In this position, the flat surfaces 13 and 15 of the top and bottom parts 11 and 14 lie against each other in such a way that a rotationally symmetrically uniform and conically tapering tip is formed. FIG. 12c shows that in the assembled state the top part 11 and the bottom part 14 have an essentially completely circular outer contour.

Figure 13:
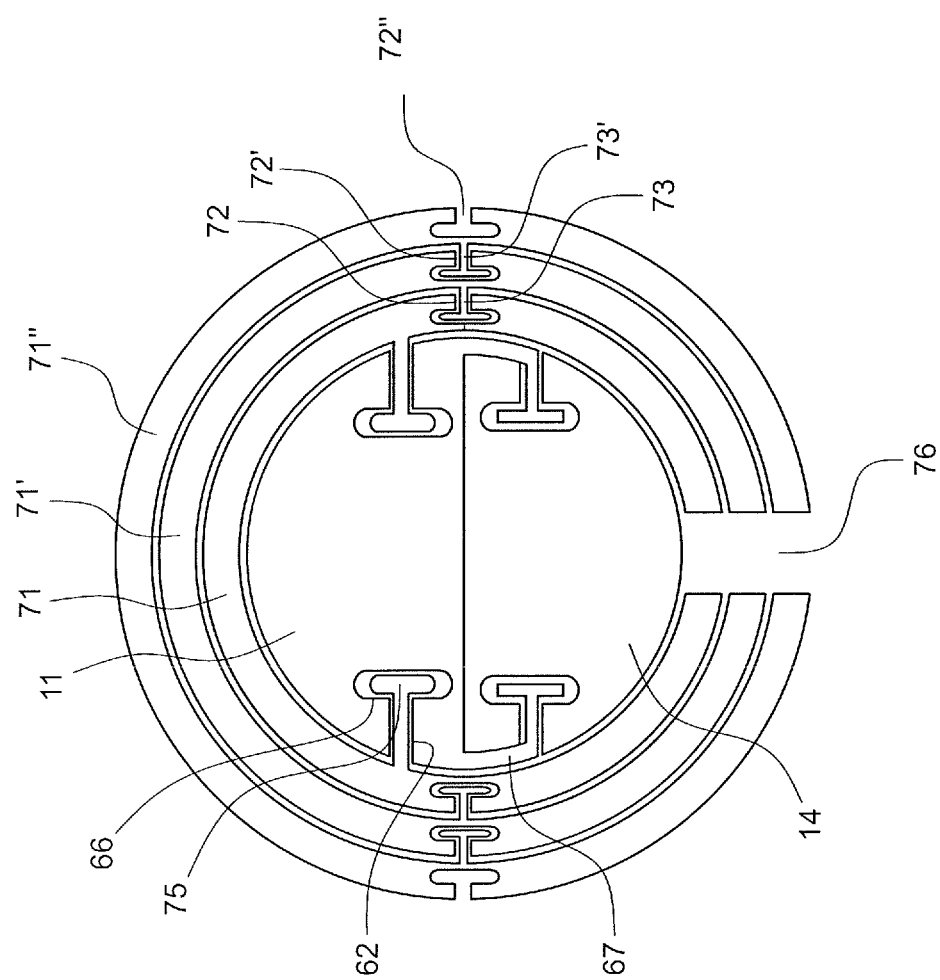
FIG. 13—a cross sectional view of the connected parts of the two-part body member in connection with three dilating cylinders.

As FIG. 13 shows, the body member 10 can be part of a telescopically adjustable arrangement. For this purpose the body member 10 is arranged within a plurality of hollow cylinders 71, 71', 71" which are movable against each other and which are connected via slidable tongue and groove connections to each other. The innermost hollow cylinder 71 has two engaging elements 75 which extend opposite each other from its inner side and which are anchored with T-shaped arms in the undercuts 66 of the grooves 62 of the top part 11 and can be displaced in the longitudinal direction of the grooves 62. In contrast to the other embodiments of the invention, not the saddle 70 engages into the outer grooves of the body member 10, but the innermost hollow cylinder 71 of the telescope arrangement. Instead, a saddle 70 according to the other embodiments of the invention can be slidably fastened in the outer grooves 72" of the outermost hollow cylinder 71". The first hollow cylinder 71 also has two opposite undercut grooves 72 on the side of its outer circumference. T-shaped arms 73 of the second hollow cylinder 71', which surrounds the first hollow cylinder 71, reach into these grooves 72. The second hollow cylinder 71' is displaceable in the longitudinal direction of the grooves 72. A third hollow cylinder 71" surrounds the second hollow cylinder 71' and has T-shaped arms 72' which are engaged in two opposite undercut grooves on the side of the outer circumference of the second hollow cylinder 71'. The third hollow cylinder 71" is displaceable with respect to the second hollow cylinder 71' in the longitudinal direction of the grooves 72'. The telescopic arrangement may have an indefinite number of further hollow cylinders, each surrounding the previous one and engaging with T-shaped arms in its outer grooves and being displaceable relative to this. The hollow cylinders 71, 71', 71", 71" each have an elongated slot 76 on their underside, which are aligned with each other. This slot is required as free space for the holding neck 40, on which the lower part 14 of the body members 10 is held. In this arrangement, the body member 10 forms the core cylinder on which the dilating cylinders 71, 71', 71" will slide on top of each other to dilate the surgical trajectory. The telescopically adjustable arrangement can be a simple mechanical holding system in which the desired positioning of the surgical device can be manually adjustable. It is also conceivable that the positioning is performed mechanically, for example by a robotic system.

The invention claimed is:
1. A surgical apparatus, for localizing and treating lesions in a brain, comprising:
 a telescopically expandable body member having an anterior end, a posterior end, and comprising a top part and a bottom part, the bottom part having at least one groove extending for a particular length in a longitudinal direction of the bottom part between said anterior end and said posterior end, the top part being placed on said bottom part and having at least one engaging element that extends into said at least one groove of the bottom part so as to mount the top part on the bottom part moveable in said longitudinal direction of the bottom part, wherein the body member has a substantially circular or polygonal cross-section in the assembled state of the bottom part and the upper-top part; the top part comprising at least one groove extending for a particular length in a longitudinal direction of the top part between said anterior end and said posterior end; the surgical apparatus further comprising a first hollow cylinder adapted to extend the range of the surgical apparatus, the first hollow cylinder being arranged around said body member and having at least one engaging element on its inner circumference, the at least one engaging element of said first hollow cylinder extending into said at least one groove of the top part so as to mount the first hollow cylinder on the body member moveable in said longitudinal direction of the top part.

2. The surgical apparatus according to claim 1, wherein said at least one groove of the bottom part comprises an inner shape and said at least one engaging element of the top part comprises an outer shape, and wherein said inner shape and said outer shape are form-locking with respect to each other and are slidingly supported on one another.

3. The surgical apparatus according to claim 2, wherein said inner shape and said outer shape form an undercut and monovariant connection between said at least one groove and said at least one engaging element.

4. The surgical apparatus according to claim 1, wherein the at least one engaging element of the top part comprises a leg extending downwardly away from said top part, and a T-shaped base element extending horizontally from the end of the leg to the inside of the top part.

5. The surgical apparatus according to claim 1, wherein said at least one groove of the bottom part comprises a block at its end facing the anterior end of the body member.

6. The surgical apparatus according to claim 1, wherein the at least one groove of the bottom part comprises an insert opening at a front face of the posterior end.

7. The surgical apparatus according to claim 1, wherein the body member is wider on the posterior end than on the anterior end.

8. The surgical apparatus according to claim 1, wherein said bottom part comprises two of said grooves, one groove on each of two opposite longitudinal outer faces of the bottom part.

9. The surgical apparatus according to claim 1, further comprising a saddle adapted to securely hold a medical device, the saddle being placed on said top part and having at least one grip that extends into said at least one groove of the top part so as to mount the saddle on the top part moveable in said longitudinal direction of the top part.

10. The surgical apparatus according to claim 1, wherein the first hollow cylinder comprises at least one groove extending for a particular length in a longitudinal direction at the outer circumference of the first hollow cylinder.

11. The surgical apparatus according to claim 10, further comprising a second hollow cylinder, the second hollow cylinder being arranged around the first hollow cylinder and having at least one engaging element on its inner circumference, the at least one engaging element of said second hollow cylinder extending into said at least one groove of the first hollow cylinder so as to mount the second hollow cylinder on the first hollow cylinder moveable in said longitudinal direction of the first hollow cylinder.

12. The surgical apparatus according to claim 11, wherein the second hollow cylinder comprises at least one groove extending for a particular length in a longitudinal direction at the outer circumference of the second hollow cylinder.

13. The surgical apparatus according to claim 12 further comprising a third hollow cylinder, the third hollow cylinder being arranged around the second hollow cylinder and having at least one engaging element on its inner circumference, the at least one engaging element of said third hollow cylinder extending into said at least one groove of the second hollow cylinder so as to mount the third hollow cylinder on the second hollow cylinder moveable in said longitudinal direction of the second hollow cylinder.

\* \* \* \* \*